United States Patent [19]

Kouda et al.

[11] Patent Number: 6,013,490

[45] Date of Patent: *Jan. 11, 2000

[54] METHOD FOR CULTIVATING APPARATUS FOR THE PRODUCTION OF BACTERIAL CELLULOSE IN AN AERATED AND AGITATED CULTURE

[75] Inventors: Tohru Kouda, Kawasaki; Yasuhisa Nagata, Yokohama; Hisato Yano; Fumihiro Yoshinaga, both of Kawasaki, all of Japan

[73] Assignee: Bio-Polymer Research Co., Ltd., Kawasaki, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/824,096

[22] Filed: Mar. 25, 1997

[51] Int. Cl.$^7$ ............................... C12P 19/12; C08B 1/00
[52] U.S. Cl. .............................. 435/101; 536/56; 536/126
[58] Field of Search ................................ 435/101; 536/56, 536/126

[56] References Cited

U.S. PATENT DOCUMENTS

| | | | |
|---|---|---|---|
| 4,256,839 | 3/1981 | Solomons et al. | 435/314 |
| 4,863,565 | 9/1989 | Johnson et al. | 162/150 |

*Primary Examiner*—Francisco Prats
*Attorney, Agent, or Firm*—Oblon, Spivak, McClelland, Maier & Neustadt, P.C.

[57] ABSTRACT

A method for the production of a bacterial cellulose by cultivating a cellulose-producing bacteria for at least a certain period of time under such an apparatus condition that an oxygen-transfer coefficient ($K_L a$) is about 25 to about 50/hr, said $K_L a$ is determined by using a simulated suspension containing 2% by weight of BC and having a plastic viscosity of 15 to 20 poise.

8 Claims, 4 Drawing Sheets

METHOD FOR CULTIVATING APPARATUS FOR THE PRODUCTION OF BACTERIAL CELLULOSE IN AN AERATED AND AGITATED CULTURE

BACKGROUND OF THE INVENTION

This invention relates to a cultivating apparatus which can achieve a specific oxygen-transfer coefficient ($K_L a$), and to a method for the production of cellulosic material (bacterial cellulose: "BC") by using microorganisms capable of producing the BC (cellulose-producing bacteria) under said specific $K_L a$ condition.

Since the BC is edible, it is utilized in the food industry. The BC's high dispersibility in water further provides it with a lot of industrial utility value, such as to maintain viscosity of food, cosmetics or coating agents, to strengthen food materials, to maintain moisture, to improve stability of food, and to be used as low-calorie additives and an emulsion stabilizer.

The BC is characterized by a sectional width of its fibrils, which is smaller by two orders of magnitude than that of other kinds of cellulose such as those derived from wood pulp.

Due to such structural and physical features of microfibrils, a homogenized BC has plenty of industrial utility as a strengthening agent for polymers, especially hydrophilic polymers. Products prepared by solidification of the homogenized BC in the form of a lump or paper show a high elastic modulus in tension due to the above feature, and are therefore expected to have excellent mechanical properties for use in various kinds of industrial materials.

Methods for the production of the BC are described in, for example, Japanese Patent Laid-Open Application Sho 62(1987)-265990, Japanese Patent Laid-Open Application Sho 63(1988)-202394 and Japanese Patent Publication Hei 6(1994)-43443.

As a nutrient medium suitable for the culture of the cellulose-producing bacteria, Schramm/Hestrin medium is known, which contains carbon source, peptone, yeast extract, sodium phosphate and citric acid (Schramm et al., J. General Biology, 11, pp.123–129, 1954). Further, it has been found that the productivity of the BC is increased by the addition of an accelerator for the cellulose production such as inositol, phytic acid and pyrroloquinoline quinone (PQQ) (Japanese Patent Publication Hei 5(1993)-1718; Mitsuo TAKAI, Japan TAPPI Journal, Vol.42, No.3, pp.237–244), carboxylic acid or their salts (Japanese Patent Laid-Open Application Hei 7(1995)-39386), invertase (Japanese Patent Laid-Open Application Hei 7(1995)-184677) and methionine (Japanese Patent Laid-Open Application Hei 7(1995)-184675) into such a nutrient medium.

The bacteria may be generally cultured in any known culture conditions such as static culture, shaken culture, and aerated and agitated culture, and in any known culture operation methods such as batch fermentation, fed batch fermentation, repeated batch fermentation and continuous fermentation.

Means for agitation include impellers (agitating blades), air-lift fermenters, pump-driven recirculation of the fermenter broth and any combination of these means.

The impellers include gate-shape impellers, turbine impellers, double helical ribbon impellers and screw impellers.

By the way, in most industrial fermentation processes, the oxygen demand for the culture is usually filled with aeration and agitation. However, an oxygen-supply capacity of fermenters restricts the productivity in many fermentation processes. Accordingly, it is considered important to investigate the factors involving the oxygen supply in the culture of the bacteria.

When the oxygen transfers from the air into the bacteria in the culture system, the oxygen-transfer from a gas phase (air bubbles) to a liquid phase may be represented by the following formula:

$$\frac{d C_L}{d t} = K_L a (C^* - C_L) \tag{I}$$

wherein $C_L$ represents dissolved oxygen concentration in the culture medium (mmol/l), t represents time (hr), $$\frac{d C_L}{d t}$$

represents a change of the dissolved oxygen concentration for a certain period of time, i.e., oxygen-transfer rate (mmol/l·hr), $K_L$ represents oxygen-transfer coefficient (cm/hr) at a liquid boundary membrane, "a" represents area of gas-liquid interface per unit volume (cm²/cm³), $C^*$ represents the dissolved oxygen concentration (mmol/l) which is in an equilibrium state with the partial pressure of oxygen in the air bubbles.

$K_L$ is a reciprocal number of resistance for the oxygen-transfer from the gas phase to the liquid phase, and ($C^*-C_L$) is considered a driving force for transferring the oxygen against the resistance. Since it is very difficult to measure $K_L$ and "a" in the fermentation system, $K_L a$ named as an oxygen-transfer coefficient is usually used. The dimension of $K_L a$ is a reciprocal number of time, and therefore generally represented as $hr^{-1}$. The oxygen-transfer coefficient indicates an oxygen-transfer capacity of a fermenter. Under the same condition, a greater value of $K_L a$ indicates a greater oxygen-transfer capacity.

When conventional batch and fed batch fermentation methods are used, in particular, under the aerated and agitated culture condition, accumulation of the BC in the culture medium due to the culture of the cellulose-producing bacteria will increase the viscosity of the culture medium at the latter half of the culture period, so that it may be considerably difficult to fully and homogeneously mix the whole of the culture system. The above difficulty will cause the lack of the oxygen-supply by aeration and reduce the production rate of BC.

The present inventors have now developed a cultivating apparatus having excellent apparatus performances on $K_L a$ indicating the oxygen-supply capacity, and has perfected the present invention.

SUMMARY OF THE INVENTION

The present invention relates to a cultivating apparatus which is provided with a gate-shape impeller and a turbine impeller within the same fermenter, or with an impeller on the horizontal axis in a fermenter.

The present invention also relates to a method for the production of BC by cultivating cellulose-producing bacteria for at least a certain period of time under such an apparatus condition that $K_L a$ is about 25/hr or more, preferably, about 25 to about 50/hr.

Each symbol in FIG. 2 to FIG. 7 means as follows:

○: gate-shape impeller+turbine impeller ("A" of FIG. 1)
▲: gate-shape impeller+turbine impeller ("B" of FIG. 1)
△: gate-shape impeller
●: turbine impeller
□: double helical ribbon impeller
■: horizontal axis-type impeller

DETAILED DESCRIPTION OF THE INVENTION

As the gate-shape impeller and turbine impeller used in the present cultivating apparatus, any conventional impeller having various shapes may be used.

The turbine impeller includes, for example, general rashtone turbine, paddle turbine without a disk, paddle turbine provided with a disk directly above said paddle, curved-paddle turbine, scaver turbine and marine impeller turbine.

In the present cultivating apparatus, the gate-shape impeller and the turbine impeller may be provided on the same axis or different axes in the same fermenter.

Figure 1A:
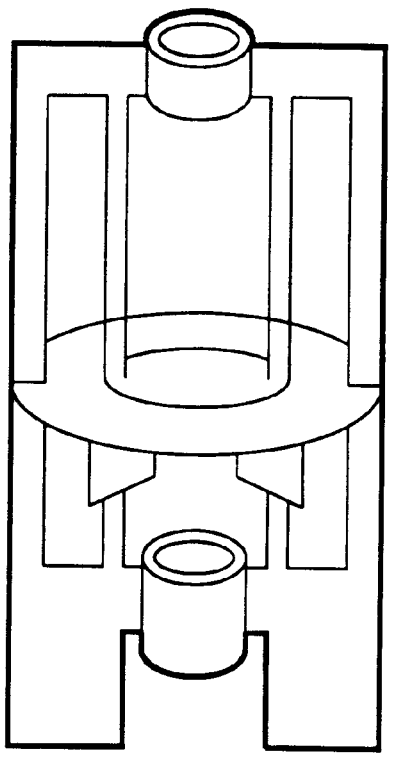
FIG. 1 shows preferred embodiments of the impellers used in the present apparatus.
Figure 1B:
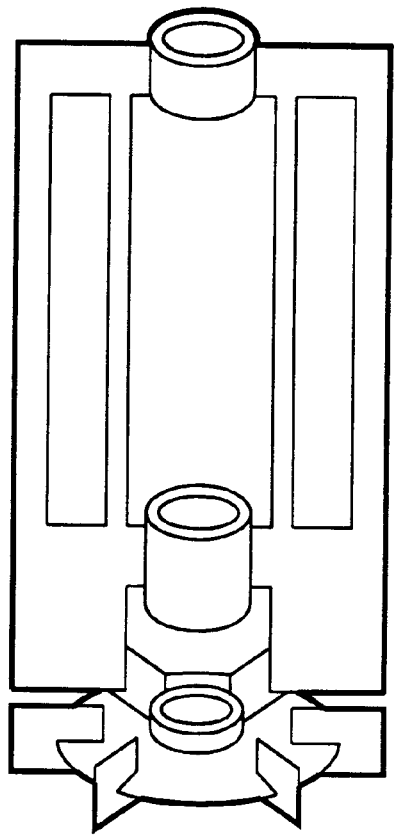

It is preferred to provide the turbine impeller within the gate-shape impeller on the same axis (A), or to provide the turbine impeller under the gate-shape impeller on the same axis (B) (See FIG. 1).

The gate-shape impeller may generate axial and radial flows, causing homogeneous mixing of the culture medium. On the other hand, the turbine impeller may finely divide the bubbles due to its partially high shearing. Accordingly, as will be described below, higher $K_La$ which has been never expected from the conventional technique can now be attained by these two kinds of the impellers provided within the same apparatus.

Further, the present invention relates to a cultivating apparatus which is provided with an impeller on the horizontal axis in a fermenter. The impeller includes any conventional impeller which has been already known as "impellers". It is possible to provide two or more of these impellers on the same horizontal axis.

This apparatus may also improve the fluidity of the culture medium, whereby higher $K_La$ can be attained. The horizontal axis may be inclined up to about 80°.

$K_La$ is an important factor in the culture and usually indicates the apparatus performances. However, $K_La$ may be varied depending on properties of the liquid to be measured, the shape of the impellers and the number of the rotation.

According to the present invention, $K_La$ may be determined as a factor directly involving the improvement of the productivity by using a simulated suspension having similar rheological properties to those of a BC culture broth to be realized, without depending on the shape or the number of the rotation of the impellers.

Determination System of $K_La$

A glass jar fermenter having a total volume of 3 liters is filled up to 60% of its total volume with a simulated suspension containing 2% by weight of BC and having a plastic viscosity of 15 to 20 poise. Nitrogen is passed through the simulated suspension under agitation to obtain the dissolved oxygen concentration of between 0 and 10% of saturation. The air having a partial oxygen pressure of 20 and 21% is then passed through the simulated suspension, and the increase of the dissolved oxygen concentration is measured by using a dissolved oxygen electrode.

$K_La$ may be calculated by using the above formula (I). Conveniently, the dissolved oxygen concentration is measured every 5 to 30 seconds, and $K_La$ is then calculated by using the following formula:

$$((DO2-DO1)/(t2-t1))/(C^*-(DO1+DO2)/2)(\text{unit: hr}^{-1}),$$

wherein DO1 represents the dissolved oxygen concentration at the time t1, DO2 represents the dissolved oxygen concentration at the time t2, and C* represents the dissolved oxygen concentration which forms an equilibrium state with the partial pressure of oxygen in bubbles.

Figure 2:
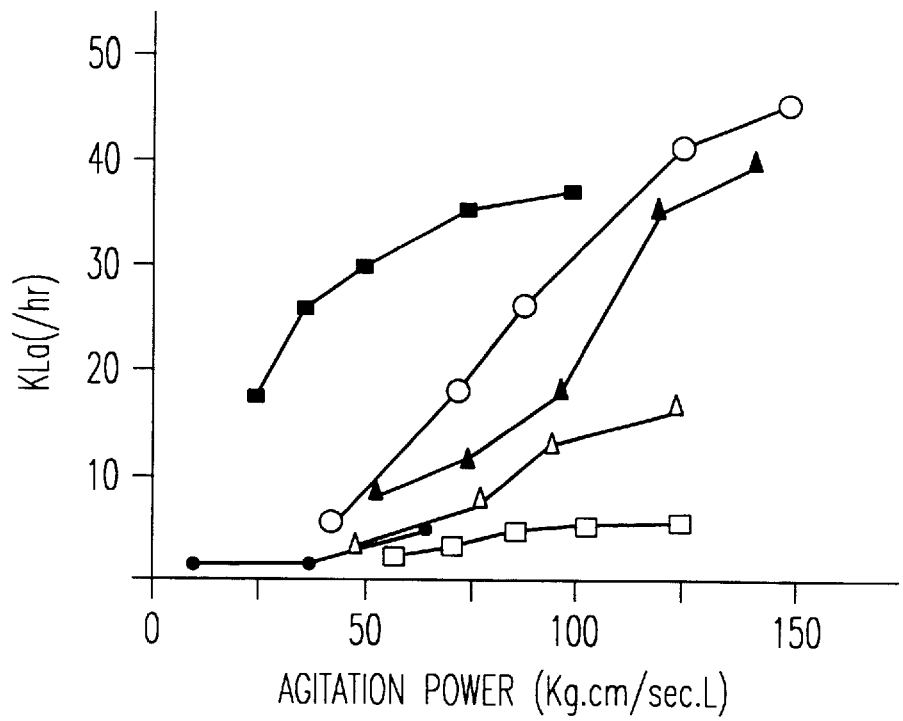
FIG. 2 shows $K_La$ achieved by various impellers.

According to the above determination system, under the agitation power in a range of 5 to 150 kg·cm/sec·L, the turbine impellers conventionally used for a general culture may give $k_La$ of 5/hr or less at the rotation of 400 to 1,200 rpm, the gate-shape impellers used in the Japanese Patent Laid-open Application Hei 5 (1993)-284990 may give $K_La$ of about 2 to about 15/hr at the same rotation range (See FIG. 2). Even if the rotation rate is further increased, $k_La$ can not be improved because the power is not sufficiently transmitted over the whole suspension.

On the contrary, the impellers used in the present cultivating apparatus can achieve $K_La$ of about 20 to about 50/hr at the rotation of 400 to 1,200 rpm. When the rotation rate is further increased, $K_La$ may be improved. However, it is economically less effective to use said higher rotation because the increment efficiency of $K_La$ for the power consumption is reduced at $K_La$ exceeding about 50/hr.

Accordingly, the present cultivating apparatus is particularly suitable for the culture system containing a viscous culture medium, for example, for the culture of the cellulose-producing bacteria.

In the present specification, the expression "such an apparatus condition that $K_La$ is about 25 to about 50/hr" means a condition that $K_La$ of about 25 to about 50/hr may be obtained when the impellers of the present cultivating apparatus is applied to the above determination system of $K_La$.

Those skilled in the art may optionally select the cultivating time and period which are controlled under the above specific apparatus condition, depending on the type of bacterial, the composition of culture media, the type of cultivating apparatus and the like. Since the viscosity of the culture medium is increased due to the accumulation of the BC, it is preferred to supply an enough amount of oxygen into the culture medium by keeping the above specific $K_La$ for a certain period of time, usually at least when the cellulose concentration in the culture medium ekceeds 5 g/L or when the BC production rate exceeds 0.2 g/L/hr. It is possible to intermittently repeat the application of this specific apparatus condition over the total culture of the bacteria.

In the preferred embodiment according to the present method, the present cultivating apparatus is used.

As already described above, the present cultivating apparatus can achieve the higher $K_L a$, even under highly viscous states exceeding 100 cp or under Bingham plastic state.

The present method can achieve an extremely higher production rate of BC.

In addition to the above culture conditions and culture operation methods, it is also possible to use for the present invention the method for the production of BC described in the Japanese Patent Laid-Open Application Hei 8(1996)-33494, wherein culture media containing bacteria are circulated between a cultivating apparatus and a separator such as a floatation equipment and an edge filter to separate the resulting BC from the bacteria and culture media in said separator, or the method for the production of BC described in Japanese Patent Laid-open Application Hei 8(1996)-33495, wherein the concentration of the BC in culture media is kept at a lower level, for example, at most 10 g/L or such a low level that the oxygen consumption rate is kept at a level above 15 mmol/L/hr by a continuous removal of the culture media from its culture system and a continuous supply of fresh culture media having almost the same volume as the removed culture media.

The cellulose-producing bacteria used in the present invention include Acetobacter strains such as *Acetobacter xylinum* subsp. sucrofermentans such as BPR 2001 strain, *Acetobacter xylinum* ATCC23768, *Acetobacter xylinum* ATCC23769, *Acetobacter pasteurians* ATCC10245, *Acetobacter xylinum* ATCC14851, *Acetobacter xylinum* ATCC11142, *Acetobacter xylinum* ATCC10821; Agrobacterium, Rhizobium; Sarcina; Pseudomonus, Achromobacter; Alcaligenes Aerobacter; Azotobacter; and Zooglea; and strains derived from those strains by using known mutagens such NTG (nitrosoguanidine).

The BPR 2001 was deposited at the National Institute of Bioscience and Human-Technology Agency of Industrial Science and Technology on Feb. 24, 1993 under accession number FERM P-13466, and then transferred on Feb. 7, 1994 to the deposit under the terms of the Budapest Treaty on the International Recognition of the Deposit of Microorganisms for the Purposes of Patent Procedure and Regulation under accession number FERM BP-4545.

The chemical treatment using mutagens such as NTG is described in, for example, Bio Factors, Vol. 1, pp.297–302 (1988) and J. Gen. Microbiol, Vol. 135, pp.2917–2929 (1989). Accordingly, those skilled in the art may obtain the present mutants in accordance with these known methods. The present mutants may be also obtained by other treatments such as application of radioactive rays.

Carbon sources in the culture media useful in the present invention include sucrose, glucose, fructose, mannitol, sorbitol, galactose, maltose, erythritol, glycerol, ethyleneglycol, ethanol and their mixtures. In addition, sucrose may be combined with starch hydrolysate containing these carbon sources, citrus molasses, beet molasses, squeezed juice from beet or sugar cane, juice from citrus and the like.

Nitrogen sources useful in the present invention include organic or inorganic ones such as ammonium salts including ammonium sulfate, ammonium chloride, ammonium phosphate; nitrates; and urea. Nitrogen-containing natural nutrients may be also used including Bacto-Peptone, Bacto-soytone, Yeast-Extract, CSL (corn steep liquor) and Bean-Condensate.

A trace amount of organic nutrients may be further added including amino acids, vitamins, fatty acids, nucleic acids, 2,7,9-tricarboxy-1H pyrrolo [2,3,5]-quinoline-4,5-dione, sulfite pulp waste liquor, lignin sulfonic acid and the like.

When the mutants with nutritional requirement for amino acids are used, such required nutrients should be supplemented in the culture media. Inorganic nutrients include phosphate salts, magnesium salts, calcium salts, iron salts, manganese salts, cobalt salts, molybdate salts, hematite salts, chelate metal salts and the like.

It is also possible to optionally supply the known accelerators for the cellulose production.

For example, when the Acetobacter is used as the cellulose-producing bacteria, a pH range for the culture is controlled between 3 and 7, preferably around 5. A culture temperature is kept in a range between 10 and 40° C., preferably between 25 and 35° C. Oxygen supply into a cultivating apparatus may contain from 1 to 100% oxygen, desirably 21 to 80%. Those skilled in the art may optionally determine the contents of these components in the culture media and the inoculation of the bacteria into the media, depending on the culture method to be used.

The BC produced in the present method may be recovered together with the bacterial cells, and then impurities other than the BC, including the bacterial cells per se, may be removed from the recovered BC.

The impurities may be almost completely removed from the BC by washing, dehydration under pressure, dilute acid washing, alkali washing, bleaching with hypochlorite soda or hydrogen peroxide, lysing with lytic enzymes such as lysozyme, treatment with surfactants such as lauryl sulfate soda or deoxycholate soda, washing under heat at a temperature range between a room temperature and 200° C., and any combination of these treatments.

The BC thus obtained according to the present invention includes cellulose, those comprising heteropolysaccharides having cellulosic main chains, and those comprising β-1,3- or β-1,2-glucan. Said heteropolysaccharides contain as components hexoses, pentoses and organic acids such as mannose, fructose, galactose, xylose, arabinose, rhamnose and glucuronic acid, as well as glucose.

These polysaccharides may be present alone or as a mixture combined each other via hydrogen bonds.

The present invention will be further illustrated by the following examples, which should not be construed to limit the scope of the present invention.

EXAMPLES

Example 1

The present method was carried out as follows by using the conventional cultivating apparatus (a gate-shape impeller, turbine impeller and double helical ribbon) having $K_L a$ of about 2 to about 15/hr measured by the $K_L a$ determination system defined above, and by using the present cultivating apparatuses having $K_L a$ of about 25 to about 50/hr under the same conditions, wherein a turbine impeller is located within a gate-shape impeller on the same axis (A), a turbine impeller is located under a gate-shape impeller on the same axis (B) and a (gate-shape) impeller is located on the horizontal axis (abscissa axis) (C).

The BPR 2001 strain (FIG. 3 and FIG. 6), BPR 3001N strain which was deposited on Jun. 10, 1994 under accession number FERM P-14361 (FIG. 4) and a new mutant derived from the BPR 2001 strain by the NTG treatment (FIG. 5 and FIG. 7) were cultured in the above cultivating apparatuses under the following conditions.

Cultivating Condition

A baffled flask (500 ml volume) containing 125 ml of CSL-Fru medium was inoculated with the bacteria such as BPR 2001 strain, and pre-cultured at 28° C. for three days under a shaken culture condition. All the above bacteria solution was then added to a jar (3 litter volume) containing 2 liters of CSL-Fru medium. The bacteria were cultured under an aerated and agitated culture condition at an aeration rate of 660 ml/minute and at an agitation rate of 400 to 1200 rpm to sufficiently supply the dissolved oxygen.

Composition of Culture Medium

CSL-Fru medium

| Fructose | 7.0 (%) |
|---|---|
| $KH_2PO_4$ | 0.1 |
| $MgSO_4 \cdot 7H_2O$ | 0.025 |
| $(NH_4)_2SO_4$ | 0.33 |
| Vitamin Mixture (see below) | 1.0 |
| Salt Mixture | 1.0 |
| CSL | 2.0 |
| pH | 5.0 |

Vitamin Mixture

| compound | mg/L |
|---|---|
| Inositol | 200 |
| Niacin | 40 |
| Pyridoxine HCl | 40 |
| Thiamine HCl | 40 |
| Ca Pantothenate | 20 |
| Riboflavin | 20 |
| p-Aminobenzonic Acid | 20 |
| Folic Acid | 0.2 |
| Biotin | 0.2 |

Figure 3:
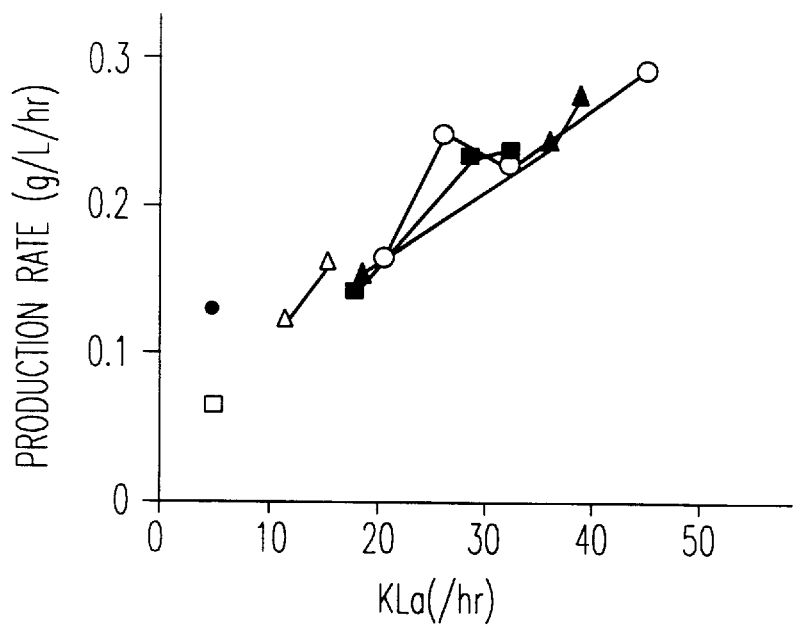
FIG. 3 shows the production rates of BC obtained by keeping $K_La$ at the highest level for a certain period of time in the cultivating apparatuses provided with the various impellers.
Figure 4:
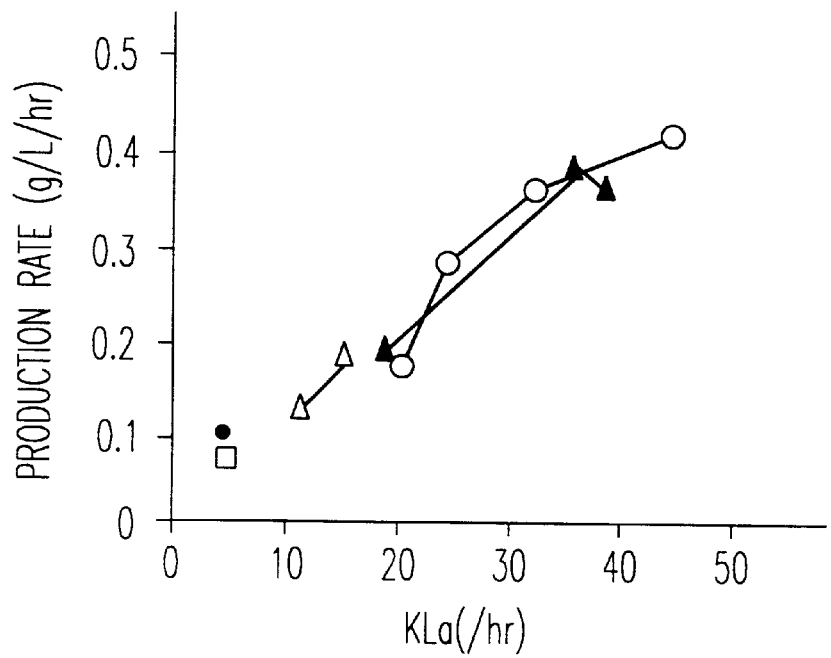
FIG. 4 shows the production rates of BC obtained by keeping $K_La$ at the highest level for a certain period of time in the cultivating apparatuses provided with the various impellers.
Figure 5:
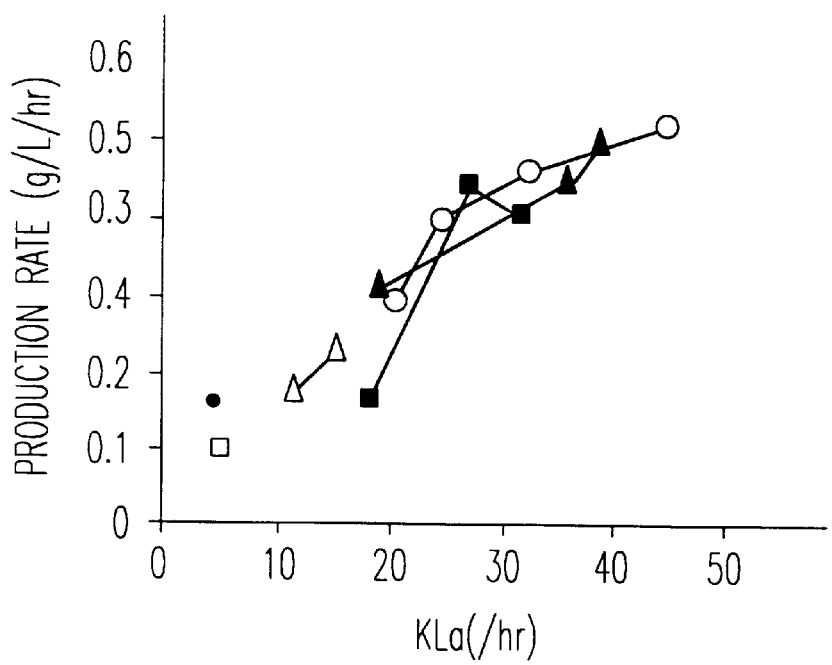
FIG. 5 shows the production rates of BC obtained by keeping $K_La$ at the highest level for a certain period of time in the cultivating apparatuses provided with the various impellers.
Figure 6:
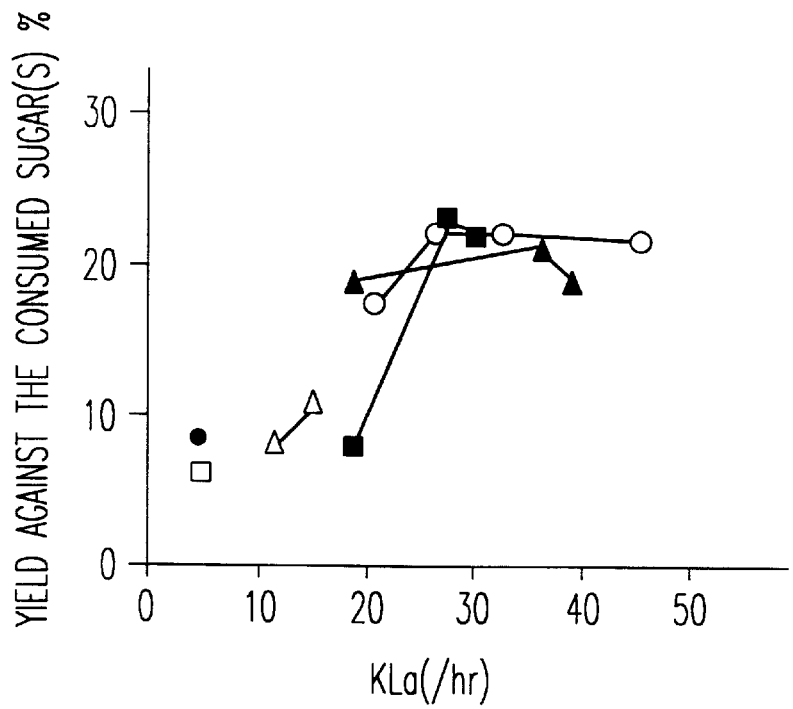
FIG. 6 shows the relation between the yields of BC against the consumed sugars and the highest $K_La$ kept for a certain period of time in the cultivating apparatuses provided with the various impellers.
Figure 7:
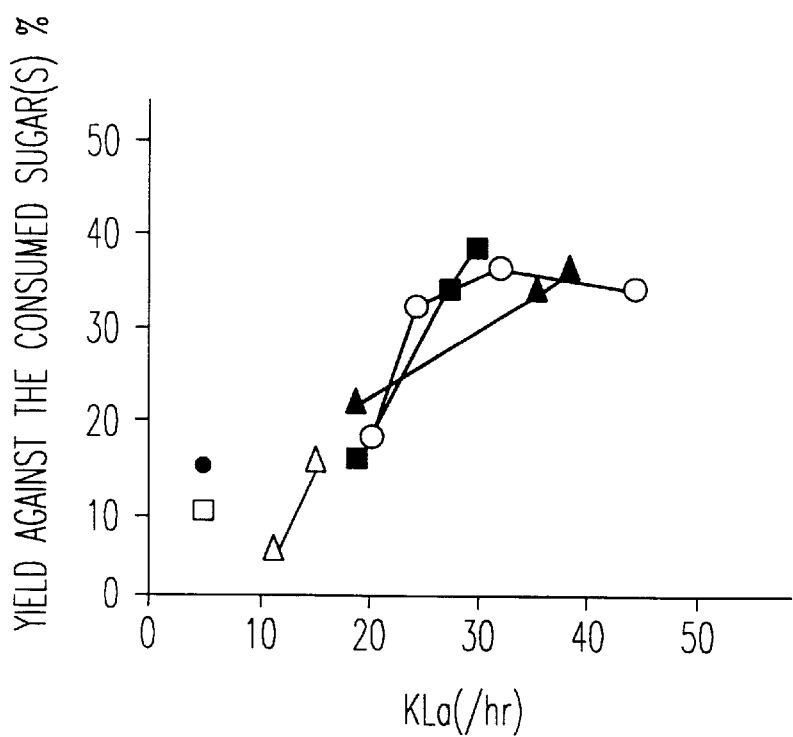
FIG. 7 shows the relation between the yields of BC against the consumed sugars and the highest $K_La$ kept for a certain period of time in the cultivating apparatuses provided with the various impellers.

The resulting production rates are shown in FIG. 3 to FIG. 5, and the yields against the consumed sugars are shown in FIG. 6 and FIG. 7.

These results demonstrate that the production rate of the BC was outstandingly increased by keeping $K_L a$ at the highest level of about 25 to 50/hr for a fixed period in the present method.

The accumulated amounts of the BC (g/L) in respective Figure were calculated as follows. After the completion of the culture, the solid contents in the jar fermenter were collected, washed with water to remove the medium components, and treated with 1 N NaOH aqueous solution at 80° C. for 20 minutes to remove the bacterial cells. The resulting cellulose was washed until the washing water became approximately neutral, and dried under vacuum at 80° C. for 12 hours to weigh the dry cellulose. The yield against the consumed sugars (%) was calculated as follows. Calculation of Yield against the Consumed Sugars (%)

$Y_{BC} = BC/(RC_{MF} - RC_{BF})*100$ $Y_{BC}$: Yield against the consumed sugars (%)

BC: Accumulated amount of BC (g/L)

$RC_{MF}$: Sugar concentration of the medium (g/L)

$RC_{BF}$: Sugar concentration of the medium after the culture (g/L)

What is claimed is:

1. A method for the production of a bacterial cellulose (BC) comprising cultivating a cellulose-producing bacterium under such apparatus conditions that the oxygen-transfer coefficient ($K_L a$) of the equation below is about 25 to about 50/hr, said $K_L a$ is determined by employing a simulated suspension containing 2% by weight of bacterial cellulose (BC) and having a plastic viscosity of 15–20 poise:

$$\frac{dC_L}{dt} = K_L a(C^* - C_L)$$

wherein $C_L$ is the dissolved oxygen concentration in the culture medium (mmol/l), t is time (hr), $dC_L/dt$ is the change in dissolved oxygen concentration over a certain period of time, $K_L$ is the oxygen-transfer coefficient (cm/hr) at a liquid boundary membrane, a is the area of gas-liquid interface per unit volume ($cm^2/cm^3$), and $C^*$ is the dissolved oxygen concentration (mmol/l) in equilibrium with the partial pressure of oxygen in air bubbles.

2. The method of claim 1, comprising conducting the cultivation in an apparatus provided with an impeller on the horizontal axis in a fermenter.

3. The method of claim 1, wherein the cellulose producing microorganism being cultured is a strain of Acetobacter, Agrobacterium, Rhizobium, Sarcina, Pseudomonus, Achromobacter, Alcaligenes, Aerobacter, Azotobacter or Zooglea.

4. The method of claim 3, wherein said strain of Acetobacter is *Acetobacter xylinum* subsp. sucrofermentans, *Acetobacter xylinum* ATCC 23768, *Acetobacter xylinum* ATCC 23769, *Acetobacter pasteurianus* ATCC 10245, *Acetobacter xylinum* ATCC 14851, *Acetobacter xylinum* ATCC 11142 or *Acetobacter xylinum* ATCC 10821.

5. The method of claim 4, wherein said cultivation occurs at a pH of 3 to 7 at a temperature in the range of 10 to 40° C. at an oxygen supply of 1 to 100%.

6. The method of claim 5, wherein said pH is about 5.

7. The method of claim 1, which further comprises conducting the cultivation in an apparatus provided with an impeller generating both axial and radial flows, and a seprate turbine impeller within the same fermenter.

8. The method of claim 7, wherein each of the impellers are rotated at a rate of 400–1200 rpm.

* * * * *